United States Patent [19]

Nielsen

[11] Patent Number: 5,693,794
[45] Date of Patent: Dec. 2, 1997

[54] CAGED POLYNITRAMINE COMPOUND

[75] Inventor: Arnold T. Nielsen, Santa Barbara, Calif.

[73] Assignee: The United States of America as represented by the Secretary of the Navy, Washington, D.C.

[21] Appl. No.: 253,106

[22] Filed: Sep. 30, 1988

[51] Int. Cl.$^6$ ............................................. C07D 259/00
[52] U.S. Cl. ........................... 540/554; 149/92; 540/556
[58] Field of Search ................................ 540/554, 556

[56] References Cited

PUBLICATIONS

J.M. Kliegman and R.K. Barnes, "Glyoxal Derivatives–I Conjugated Aliphatic Diimines From Glyoxal and Aliphatic Primary Amines," *Tetrahedron*, vol. 26 (1970), pp. 2555–2560.

J.M. Kliegman and R.K. Barnes, "Glyoxal Derivatives–II. Reaction of Glyoxal With Aromatic Primary Amines," *Journal Organic Chemistry*, vol. 35 (1970), pp. 3140–3143.

J.M. Edwards, U. Weiss, R.D. Gilardi, and I.L. Karle "Formation of a Heterocyclic Cage Compound From Ethylenediamine and Glyoxal," *Chemical Communications*, (1968), pp. 1649–1650.

R.D. Gilardi, "The Crystal Structure of $C_{10}H_{14}N_4O_2$, a Heterocyclic Cage Compound," *Acta Chystallographica*, vol. B28, Part 3 (Mar. 1972), pp. 742–746.

A.T. Nielsen and R.A. Nissan, "Polynitropolyaza Caged Explosives—Part 5," *Naval Weapons Center Technical Publication 6692* (Publication Unclassified), China Lake, Ca., Mar. 1986, pp. 10–23.

*Primary Examiner*—Richard D. Lovering
*Attorney, Agent, or Firm*—Melvin J. Sliwka; Stephen J. Church

[57] ABSTRACT

A new compound, 2,4,6,8,10,12-hexanitro-2,4,6,8,10,12-hexaazaisowurtzitane (2,4,6,8,10,12-hexanitro-2,4,6,8,10,12-hexaazatetracyclo[5.5.0.0$^{5,9}$.0$^{3,11}$]dodecane) is disclosed and a method of preparation thereof. The new compound is useful as a high energy, high density explosive.

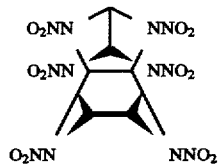

28 Claims, No Drawings

CAGED POLYNITRAMINE COMPOUND

BACKGROUND OF THE INVENTION

1. Field of the Invention

This invention relates to polyaza caged molecules. More particularly, the invention relates to polyaza caged molecules having the hexaazaisowurtzitane caged ring system, including one with nitro groups attached to each nitrogen atom, and a method for producing the same, useful as an explosive.

2. Description of the Related Art

Known polynitramines such as 1,3,5-trinitro-1,3,5-hexahydrotriazine (RDX) and 1,3,5,7-tetranitro-1,3,5,7-tetraazacyclooctane (HMX) are high-energy, high-density explosive compounds (R. Meyer, "Explosives," Third edition, VCH Publishers, Weinheim, Germany, 1987). They can be prepared by nitrolysis of hexamine with nitric acid and other similar procedures. Stable polynitramines having energy and density greater than that of HMX were unknown until the present synthesis of a new class of explosives described as caged polynitramine.

SUMMARY OF THE INVENTION

According to this invention, 2,4,6,8,10,12-hexanitro-2,4,6,8,10,12-hexaazaisowurtzitane (HNIW) is prepared starting with benzylamine and glyoxal which are condensed in a suitable solvent in the presence of a catalyst to produce hexabensylhexaazaisourtzitane(HBIW). The hexabenzy-hexaazaisourtzitane (HBIW) is reductively acylated in the presence of a catalyst in a second step to produce dibenzyltetraacetylhexaazaisowurtzitane (TAIW). Finally, in the last step, dibenzyltetraacetylhexaazaisowurtzitane (TAIW) is sequentially debenzylated and nitrated to produce 2,4,6,8,10,12-hexanitro-2,4,6,8,10,12 hexaazaisowurtzitane (HNIW).

DESCRIPTION OF THE PREFERRED EMBODIMENT

The synthesis of the first isolated intermediate compound, hexabenzylhexaazaisowurtzitane (HBIW), involves condensation of benzylamine with glyoxal (40% aqueous solution) in aqueous acetonitrile or methanol solvent with formic acid catalyst at 0° to 250° C. The best yield obtained (81%) requires slow addition of the aqueous glyoxal (1.0 mole-equivalent) to a solution of benzylamine (slightly more than 2 mole-equivalents) and formic acid (slightly more than 0.2 mole-equivalent) in aqueous acetonitrile, while keeping the temperature at 0° to 250° C. The optimum addition time for the aldehyde under these conditions is about one hour. After addition of all the glyoxal solution is complete, the reaction mixture is allowed to stand at ambient temperature (250° C.) overnight (16 to 18 hours) to complete the formation of the product which rapidly precipitates from the reaction mixture in rather pure form. The reaction to form hexabensyl-hexaazaisourtzitane (HBIW) is virtually over within a few hours. Prolonged standing may produce slightly higher yields without altering the purity of the product. The hexabenzylhexaazaisowurtzitane (HBIW)is isolated by suction filtration, followed by washing with cold acetonitrile or methanol and drying in air. The yields of the unrecrystallized product are 80 to 81%. The crude product is recrystallized from boiling acetonitrile to produce colorless crystals with a melting point of 153° to 157° C. (90% recovery).

Organic acid catalysts other than formic acid may be employed, such as acetic acid; the yield is decreased if more or less than 0.1 mole-equivalent of formic acid (relative to one mole-equivalent of amine) is employed. The reaction time is accelerated by heating, but yields of hexabenzyl-hexaazaisowurtzitane (HBIW) are not increased; excessive heating is undesirable. Other solvents may be employed (methanol, ethanol, propnol) but offer no advantages over acetonitrile.

The structure of hexabenzylhexaazaisowurtzitane (HBIW):

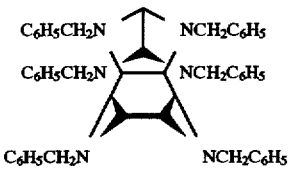

is supported by its $^1$H and $^{13}$C NMR and mass spectra. The X-ray crystal structure of the corresponding hexa(4-methoxybenzyl)hexaazaisowurtzitane, confirms the structure of the ring system.

Several other benzylamines have been successfully condensed with glyoxal to produce substituted hexabenzyl-hexaazaisowurtzitanes (with comparable yields), including 4-methoxy-, 3,4-dimethoxy-, 4-methyl-, 4-isopropyl-, 2-chloro-, and 4-chlorobenzylamines.

The second isolated intermediate compound in the reaction sequence leading to 2,4,6,8,10,12-hexanitro-2,4,6,8,10,12-hexaazaisowurtzitane (HNIW) is 4,10-dibenzyl-2,6,8,12-tetraacetyl- 2,4,8,8,10,12-hexaazaisowurtzitane (TAIW). It is prepared by reductive acetylation of pure hexabenzyl-hexaazaisowurtzitane (HBIW) in acetic anhydride solvent with hydrogen (Pd/C, 1 to 50 psi, –40° to 30° C., 2 to 24 hours) using a Parr shaker. For maximum yields, the reaction requires an acid promoter. Acids such as $H_2SO4$, HCl, or HBr (not HI) may be added directly to the reaction mixture before hydrogenation is started. Best results have been obtained with HBr. It was found most convenient to introduce the HBr in the form of bromobenzene, acetyl bromide, benzyl bromide, or other bromine containing compounds, which are dehydrohalogenated during the hydrogenation to form the HBr. The HBr reacts with the acetic anhydride to form acetyl bromide. The concentration of HBr is critical; maximum yields were obtained at HBr concentrations of about one-eighth the number of moles of hexabenzyl-hexaazaisowurtzitane (HBIW). The amount of hydrogenation catalyst, type of catalyst, and concentration of palladium on the carbon support have been varied. Palladium on charcoal is preferred over palladium metal alone. The catalyst gives best results when generated by reduction of palladium hydroxide on carbon (Pearlman's catalyst) and used in a ratio of about one-fourth the weight of hexaben-zylhexaazaisowurtzitane (HBIW). Dry palladium on charcoal (3–20%) may also be used but gives lower yields (40–50%). The reaction is continued until hydrogen uptake ceases (about 6 hours), but is usually continued overnight. The solid product, dibenzyltetraacetylhexaazaisowurtzitane (TAIW), is unaffected by the prolonged reaction time. The isolation of the product involves cooling the reaction mixture to 25° C. ( if an exotherm has occurred), followed by filtration of the catalyst mixed with most of the product. Some of the product remains in the acetic anhydride filtrate. The product (mixed with catalyst) may be recovered by extraction of the mixture with boiling chloroform. The acetic anhydride solution is concentrated under reduced pressure and the residue triturated with acetonitrile to yield the dibenzyltetraacetylhexaazaisowurtzitane (TAIW) product.

The total yield of solid product is about 60–65%. The compound may be recrystallized from acetonitrile or chloroform. The crude product is quite pure and usually may be used for the next step without further purification. The structure of dibenzyltetraacetylhexaazaisowurtzitane (TAIW):

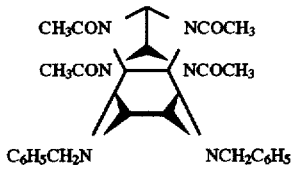

is supported by its $^1$H NMR, mass spectra and chemical behavior, (conversion into dinitrosotetraacetylhexaazaisowurtzitane and dinitrotetraacetylhexaazaisowurtzitane [in structure number 2, above, $C_6H_5CH_2$=NO and $NO_2$ respectively]; the X-ray crystal structure of the latter compound has been established).

The final reaction sequence leading to the fully nitrated solid explosive compound, 2,4,6,8,10,12-hexanitro-2,4,6,8, 10,12-hexaazaisowurtzitane (HNIW), proceeds from the precursor 4,10-dibenzyl-2,6,8,12-tetraacetyl-2,4,8,8,10,12-hexaazaisowurtzitane (TAIW) in a two-part reaction sequence. The reaction is conducted employing a suspension of the tetraacetyl precursor in sulfolane containing a small amount of water. The first part of the reaction is a nitrosative debenzylation performed at 25°–60° C. by adding nitrosonium tetrafluoroborate, ($NOBF_4$), which oxidizes the benzyl groups. In the second part of the reaction, a nitration occurs with nitronium tetrafluoroborate ($NO_2BF_4$) which is added to fully nitrate the ring at 25°–60° C. to produce hexanitrohexaazaisowurtzitane (HNIW). The $NO_2BF_4$ also reacts with benzaldehyde (which is formed) to oxidize and nitrate it to 3-nitrobenzoic acid (which may be isolated from the reaction mixture), a process which consumes four mole-equivalents of $NO_2BF_4$ and produces $NOBF_4$ (two mole-equivalents) which precipitates from solution and may be recovered from the reaction by filtration. Additional $NOBF_4$ may be recovered by passing nitrogen dioxide ($NO_2$) into the reaction mixture prior to the water quenching step. The reaction mixture containing suspended $NOBF_4$, or the sulfolane solution filtrate remaining after filtration of the $NOBF_4$, is treated with 15 times its volume of water, keeping the temperature below 25° C. The hexanitrohexaazaisowurtzitane (HNIW) precipitates from the reaction mixture as an amorphous solid which retains approximately 1% water after drying in ambient air. The crude product obtained (93–97% yield) is very pure. It is crystallized by dissolving it in ethyl acetate, followed by flash filtration through a short column of silica gel to remove traces of impurities. The ethyl acetate filtrate containing hexanitrohexaazaisowurtzitane (HNIW) is poured into chloroform to precipitate hexanitrohexaazaisowurtzitane (HNIW) in its anhydrous crystalline beta-form (92–96% recovery); d=1.98 g/cm$^3$; the particle size of the crystals may be adjusted by altering the volumes of the solvents and their temperatures at the time of mixing. The structure of 2,4,6,8,10,12-hexanitro-2,4,6,8,10,12-hexaazaisowurtzitane (HNIW):

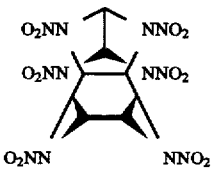

is supported by its $^1$H NMR spectrum and established by X-ray crystallography. A hemihydrate of the alpha-form, d=1.96 g/cm$^3$, may be isolated by crystallization from 70% nitric acid. Crystallization of the product from benzene also leads to an anhydrous beta-form, d=1.98 g/cm$^3$. Occasionally the crude hexanitrohexaazaisowurtzitane (HNIW) is isolated as a sulfolane adduct which is readily decomposed in boiling water to yield sulfolane-free hexanitrohexaazaisowurtzitane (HNIW).

The compound, 2,4,8,8,10,12-hexanitro-2,4,8,8,10,12-hexaazaisowurtzitane (HNIW), may be prepared by carrying out the three-step procedure set forth in the following example.

EXAMPLE

Step 1

Preparation of 2,4,6,8,10,12-hexabenzyl-2,4,6,8,10,12-hexaazatetracyclo[5.5.0.0$^{5,9}$.0$^{3,11}$]dodecane (2,4,6,8,10,12-hexabenzyl-2,4,6,8,10,12-hexaazaisowurtzitane) (HBIW).

Glyoxal (72.5 g of 40% aqueous solution, 0.50 mole) was added drop-wise to a solution of benzylamine (117.9 g, 1.10 mole), water (100 mL), and formic acid (88%, 5.76 g, 0.110 mole) in acetonitrile (1100 mL) during one hour, keeping the temperature below 20° C. The addition funnel was rinsed with 10 mL of water. After standing at 25° C. overnight (16–18 hours), the precipitated product was removed by filtration and washed with cold acetonitrile; yield 96.0 g (81.3%) of 2,4,6,8,10,12-hexabenzyl-2,4,6,8,10,12-hexaazaisowurtzitane; mp 150° to 152° C. Recrystallization from acetonitrile yielded a product with a melting point of 153° to 157° C. (90% recovery of colorless prisms); IR (KBr) shows absence of NH, C=O; CH bands are found at 2949, 2830, 2750 cm$^{-1}$; $^1$H NMR (CDCl$_3$); (IBMMR-80); delta 7.20 to 7.24 (m, 30 H, phenyl CH), 4.16 (s, 4 H, CH$_2$), 4.09 (s, 8 H, CH$_2$), 4.03 (s, 4 H, CH), 3,59 (s, 2, H, CH) ppm; $^{13}$C NMR (acetone-d$_6$) (IBMNR-80): delta 141.34, 129.67, 128.82, 128.51, 127.11 (phenyl carbons), 80.94, 77.53 (1:2 intensity ratio, C of caged ring), 57.29, 56.62 (1:2 ratio, exocyclic benzyl carbons; assignments confirmed by uncoupled spectra) ppm; mass spectrum (CI, CH$_4$) m/e 709 (MH$^+$, 0.6), 618 (0.7), 473 (0.7), 237 (100); EI 91 (100). Analysis calculated for C$_{48}$H$_{48}$N$_6$: C, 81.32; H, 6.83; N, 11.86. Found C, 81.49; H, 6.91; N, 11.84.

Step 2

Preparation of 4,10-dibenzyl-2,6,8,12-tetraacetyl-2,4,6,8,10,12-hexaazaisowurtzitane (4,10-dibenzyl-2,6,8,12-tetraacetyl-2,4,6,8,10,12-hexaazatetracyclo[5.5.0.$^{5,9}$.0$^{3,11}$] dodecane (TAIW).

A mixture of pure 2,4,6,8,10,12-hexabenzyl-2,4,6,8,10, 12-hexaazaisowurtzitane (HBIW) (150 g, 0.212 mole), acetic anhydride (500 mL., 5.3 moles), Pearlman's palladium hydroxide on charcoal catalyst (37.5 g containing 20% palladium on a dry-weight basis) and bromobenzene (4.2 g, 26.5 millimoles) was shaken in a 2.5-liter bottle in a Parr apparatus (50 psi, 10°–300° C., 18 hours). After cooling to 25° C. the catalyst, mixed with product, was removed by filtration and extracted with two or three 2-liter portions of boiling chloroform. Concentration of the extract yielded crude dibenzyltetraacetylhexaazaisowurtzitane (TAIW), which was triturated with acetonitrile and filtered to yield pure dibenzyltetraacetylhexaazaisowurtzitane (TAIW). The acetic anhydride filtrate was concentrated under reduced pressure, at a temperature range of 30°–70° C., to remove volatiles; the residue was triturated with acetonitrile to yield more dibenzyltetraacetylhexaazaisowurtzitane (TAIW). The combined yield was 69.0 g (63.2%) of the solid dibenzyltetraacetylhexaazaisowurtzitane (TAIW) compound with a melting point of 315° to 325° C. Recrystallization from acetonitrile yielded small colorless prisms with a melting point of 322° to 323° C;. $^1$H NMR (DMSO-$d_6$) delta 7.38, 7.31 (m, 10 H, Cells), 6.50 (broad s, 2 H, CH), 5.43 (broad s, 4 H, CH), 4.07 (s, 4 H, CH$_2$), 2.03 (broad m, 12 H, CH$_3$); mass spectra (CI, CH$_4$), m/e 517 (MH+, 100) 518 (32), 545 (M+29, 18), 476 (5), 455 (11), 363 (10), 111 (21). Analysis calculated for $C_{28}H_{32}N_6O_4$: C, 65.10; H, 6.24; N, 16.27. Found: C, 65.18; H, 6.50; N, 16.03.

Step 3

Preparation of hexanitrohexaazaisowurtzitane (2,4,6,8,10,12-hexanitro-2,4,6,8,10,12-hexaazaisowurtzitane or 2,4,6,8,10,12-hexanitro-2,4,6,8,10,12-hexaazatetracyclo [5.5.0.0$^{5,9}$.0$^{3,11}$]dodecane) (HNIW).

To a mixture of pure 4,10-dibenzyl-2,6,8,12-tetraacetyl-2,4,6,8,10,12-hexaazaisowurtzitane (TAIW) (15.49 g, 0.03 mole), water (1.08 g, 0.06 mole) and sulfolane (300 mL) in a 5-1, 3-necked, round-bottomed flask, nitrosonium tetrafluoroborate (14.02 g, 0.12 mole or 10.5 g, 0.09 mole) was added over a 30 minute time period while cooling, keeping the temperature below 25° C. The mixture, with a Drierire tube attached, was stirred mechanically, first at 25° C. for one hour and then at 55°–60° C. for one hour. The clear yellow-orange solution was then cooled to 25° C.; nitronium tetrafluoroborate (47.8 g, 0.36 mole) was added rapidly, keeping the temperature below 25° C. The mixture was stirred at 25° C. for 2 hours and at 55°–60° C. for 2 hours to produce a white solid, nitrosonium tetrafluoroborate (NOBF$_4$), suspended in a yellow solution. The NOBF$_4$ may be removed by filtration, or the mixture may be cooled to below 10° C. with an ice bath, and water (4.5 liters) slowly added, keeping the temperature below 25° C.; during addition of the water the mixture changed color to green, then yellow, and brown fumes evolved. The temperature was maintained at 25° C. with continuous stirring for 3–18 hours, during which time a white precipitate was produced. (In an alternate work-up procedure the precipitated NOBF$_4$ was recovered by filtration prior to quenching the sulfolane solution filtrate with water. Even more NOBF$_4$ may be recovered by passing nitrogen dioxide (NO$_2$) gas into the sulfolane solution prior to water treatment.) The mixture was filtered and the precipitated solid product was washed several times with water to yield 12.78 g of hydrated (<1% H$_2$O), amorphous crude hexanitrohexaazaisowurtzitane (HNIW); $^1$H NMR data indicate greater than 99% purity of a dried sample of this crude sample. The crude product was dissolved in 40 mL of ethyl acetate and filtered through a short silica gel column and washed with ethyl acetate to yield a clear, pale-yellow solution. The solution was poured into chloroform (500 mL) to precipitate 11.9 g (90.5%) of pure hexanitrohexaazaisowurtzitane (HNIW) in the anhydrous beta-crystalline form (small rhombic crystals, density 1.98 g/cm$^3$), mp 260° C. (decomposition) with phase changes at 185° and 230° C. (formation of gamma and delta forms, respectively, of hexanitrohexaazaisowurtzitane (HNIW). Analysis calculated for $C_6H_6N_{12}O_{12}$: C, 16.45; H, 1.38; N, 38.36 Found: C 16.59; H, 1.35; N, 38.18.

Occasionally the crude product was isolated (after quenching with water) as a disulfolan adduct of hexanitrohexaazaisowurtzitane (HNIW) (very pale yellow crystals with a melting point of 92° to 100° C.). Analysis calculated for $C_6H_6N_{12}O_{12} \cdot 2\, C_4H_8SO_2$: C, 24.78; H, 3.27; N, 24.77; S, 9.45. Found: C, 24.88; H, 3.26; N, 24.51; S, 9.35.

The disulfolane adduct was decomposed by heating with stirring (using a hot water bath), with distilled water (15 mL/g) at 95° C. for 10 minutes, then cooled to 0° C. After standing for 1–6 hours, the mixture was filtered and washed with cold water to Field amorphous crude hydrated hexanitrohexaazaisowurtzitane (HNIW) (<1% H$_2$O). A crystalline hemihydrate of the alpha-form of hexanitrohexaazaisowurtzitane (HNIW) was obtained by recrystallization from 70% nitric acid (80 to 85% recovery) to yield chunky rhombic crystals of the hemihydrate (alpha-form) with a melting point of 260° C. (decomposition). Analysis calculated for $C_6H_6N_{12}O_{12} \cdot 0.5\, H_2O$: C, 16.12; Hi 1.58; N, 37.58. Found: C, 16.10; H, 1.46; N, 37.31.

The anhydrous beta-form of hexanitrohexaazaisowurtzitane (HNIW) was also obtained by recrystallization from benzene to yield needle prisms of the anhydrous form (beta-form) with a melting point of 260° C. (decomposition) with phase changes to gamma and delta-forms at 185° and 230° C., respectively; density 1.98 g/cm$^3$ (determined by X-ray crystallography); $^1$H NMR (acetone-$d_6$) delta 8.33 (s, 4 H, CH), 8.18 (s, 2 H, CH); $^{13}$C NMR (acetone-$d_6$) delta 75.29 (2 C), 72.13 (4 C); mass spectra (CI, CH$_4$) m/e 467 (M+29, 24%), 439 (M+1, 30), 347 (26), 301 (28), 255 (14), 209 (18). Analysis calculated for $C_6H_6N_{12}O_{12}$: C, 16.45; H, 1.38; N, 38.36. Found: C, 16.49; H, 1.35; N, 38.02.

SUMMARY OF PROPERTIES

Appearance: alpha-modification, colorless rhombic prisms beta-modification, colorless needles or chunky prisms Molecular formula: $C_6H_6N_{12}O_{12}$ Molecular weight: 438.2

Oxygen balance (CO$_2$ and H$_2$O): −11.0%

Nitrogen percentage: 38.36

Detonation velocity (calculated): 9.38 mm/micro-second

Detonation pressure (calculated): 428 Kbar

Heat of formation (observed): +228 cal/g

Melting point: 260° C. (decomposition with phase changes to gamma-modification at 185° C. and to delta-modification at 230° C.)

Density (observed): alpha-modification 1.97 g/cm$^3$ beta-modification 1.98 g/cm$^3$ Impact sensitivity (H$_{50}$) using 2.5 kg type 12 tool: 17–21 cm (alpha or beta-modification)

Friction sensitivity: 50% point: 902 lb (beta-modification)

Electrostatic sensitivity: 10/10 no fires (0.25 Joule) (alpha-modification)

The compound, 2,4,6,8,10,12-hexanitro-2,4,6,8,10,12-hexaazaisowurtzitane (HNIW), may be utilized as an explosive in the same manner that other solid, crystalline explosive materials are used. The energy of the compound is superior to that of HMX, which has a detonation velocity of 9.1 mm/microsecond and a detonation pressure of 390 Kbar. The density of the compound is also greater than that of HMX (1.90 g/cm$^3$). The compound is very stable to heat. It does not react readily with protic solvents such as water, unlike Sorguyl (tetranitroglycoluril) or hexanitrobenzene. On the other hand, the compound may be recrystallized from boiling water or boiling nitric acid. Additionally, the compound may be used as an oxidizer in solid fuel propellants.

Modifications and variations of the present invention are possible. It should be understood that, within the scope of the appended claims, the invention may be practiced otherwise than as specifically described.

What is claimed is:

1. A compound 2,4,6,8,10,12-hexanitro-2,4,6,8,10,12-hexaazaisowurtzitane (HNIW), with the structure:

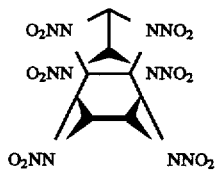

2. A method of preparing 2,4,6,8,10,12-hexanitro-2,4,6,8,10,12-hexaazaisowurtzitane (HNIW) comprising the steps of:
   A. converting stoichiometric amounts of starting materials benzylamine and glyoxal at a sufficient temperature into 2,4,6,8,10,12-hexabenzyl-2,4,6,8,10,12-hexaazaisowurtzitane (HBIW) through condensation in a suitable solvent in the presence of an organic acid catalyst;
   B. reductively acylating 2,4,6,8,10,12-hexabenzyl-2,4,6,8,10,12-hexaazaisowurtzitane (HBIW) with an acid promoter and a metal hydrogenation catalyst to form 4,10-dibenzyl-2,6,8,12-tetraacetyl-2,4,6,8,10,12-hexaazaisowurtzitane (TAIW); and
   C. forming a suspension of said 4,10-dibenzyl-2,6,8,12-tetraacetyl-2,4,6,8,10,12-hexaazaisowurtzitane (TAIW) in an aqueous sulfolane solution and sequentially debenzylating and nitrating to produce said 2,4,6,8,10,12-hexanitro-2,4,6,8,10,12-hexaazaisowurtzitane (HNIW).

3. The method of claim 2 wherein said benzylamine in step A is selected from a group of benzylamines consisting of 4-methylbenzylamine, 4-isopropylbenzylamine, benzylamine, 4-methoxybenzylamine, 3,4-dimethoxybenzylamine, 2-chlorobenzylamine, and 4-chlorobenzylamine.

4. The method of claim 2 wherein said benzylamine of step A is a methylamine substituted derivative of an aromatic heterocyclic compound selected from the group consisting of thiohene, furan, pyran, pyrrole, imidazole, pyrazole, isothiazole, isoxazole, pyridine, pyrazine, indole, indolizine, quinoline, and furazan.

5. The method of claim 2 wherein said stoichiometric amounts of starting materials in step A vary from one part benzylamine to one part glyoxal, to about four parts benzylamine to one part glyoxal.

6. The method of claim 2 wherein said glyoxal in step A is added as an aqueous solution at a rate in the range of about 0.01 mole per hour to about 1 mole per hour for a reaction on a 1 mole scale.

7. The method of claim 2 wherein said temperature sufficient to convert benzylamine and glyoxal in step A is in the range from about 0° C. to about 80° C. to prevent formation of by-products.

8. The method of claim 2 wherein said suitable solvent in step A is aqueous acetonitrile.

9. The method of claim 2 wherein said suitable solvent in step A is aqueous alcohols having 1 to 4 carbon atoms, said alcohols consisting of methanol, ethanol and propanol.

10. The method of claim 2 wherein said suitable solvent in step A is a mixture of aqueous acetonitrile and aqueous alcohol.

11. The method of claim 2 wherein said organic acid catalyst in step A is selected from the group of acids consisting of formic, acetic, and other carboxylic acid of two or more carbon atoms.

12. The method of claim 2 wherein the acylating agent in step B is acetic anhydride.

13. The method of claim 2 wherein the acylating agent in step B is selected from the group of acids consisting of propionic, butyric, pentanoic, and benzoic acid.

14. The method of claim 2 wherein said acid promoter in step B is an acid selected from the group consisting of Sulfuric, Hydrochloric and Hydrobromic acid.

15. The method of claim 2 wherein said acid promoter in step B is selected from the bromine group consisting of bromo-benzene, benzyl bromide, acetyl bromide, other easily hydrogenated brominated organic compound, which produces hydrobromic acid, and hydrobromic acid itself.

16. The method of claim 2 wherein said metal catalyst in step B is palladium on charcoal prepared by hydrogenation of palladium hydroxide on charcoal.

17. The method of claim 2 wherein said dibenzyltetraacetylhexaazaisowurtzitane obtained in step B is removed by extraction with a solvent consisting of hot chloroform, methylene chloride or acetonitrile.

18. The method of claim 2 wherein said dibenzyltetraacetylhexaazaisowurtzitane obtained in step B is filtered out of solution along with said metal catalyst and the filtrate concentrated under reduced pressure and the residue triturated with acetonitrile to yield dibenzyltetraacetylhexaazaisowurtzitane.

19. The method of claim 2 wherein said aqueous solvent solution in step C is sulfolane containing a small amount of water.

20. The method of claim 2, step C, wherein said dibenzyltetraacetylhexaazaisowurtzitane in said aqueous sulfolane solution is stirred with nitrosonium tetrafluoroborate at 25°–60° C. and then stirred with nitronium tetrafluoroborate at 25°–60° C. to form the product, 2,4,6,8,10,12-hexanitro-2,4,6,8,10,12-hexaazaisowurtzitane.

21. The method of claim 20 wherein dibenzyltetraacetylhexaazaisowurtzitane is replaced by dinitrosotetraacetylhexaazaisowurtzitane.

22. The method of claim 20 wherein dibenzyltetraacetylhexaazaisowurtzitane is replaced by dinitrotetraacetylhexaazaisowurtzitane.

23. The method of claim 20 wherein the number of mole-equivalents of nitrosonium tetrafluoroborate relative to the number of moles of dibenzyltetraacetylhexaazaisowurtzitane is varied from 2 to 14.

24. The method of claim 20 wherein the number of mole-equivalents of nitronium tetrafluoroborate relative to the number of moles of dibenzyltetraacetylhexaazaisowurtzitane is varied from 6 to 20.

25. The method of claim 2, step C, wherein the reaction mixture containing the product, 2,4,6,8,10,12-hexanitro-2,4,6,8,10,12-hexaazaisowurtzitane, is poured into a large volume of water and said product is removed by filtration and washed with water.

26. The method of claim 2, step C, wherein the product, 2,4,6,8,10,12-hexanitro-2,4,6,8,10,12-hexaazaisowurtzitane is crystallized to any desired size or crystalline modification (anhydrous or hydrated forms) by crystallization from benzene, ethanol, dichloroethane, acetic acid, nitric acid, ethyl acetate, chloroform, mesitylene, or mixtures of these and other suitable solvents.

27. A method of producing the alpha-form of the product, alpha-2,4,6,8,10,12-hexanitro-2,4,6,8,10,12-hexaazaisowurtzitane, comprising the steps of:

A. reacting 4,10-dibenzyl-2,6,8,12-tetraacetyl-2,4,6,8,10,12-hexaazaisowurtzitane sequentially with nitrosonium tetrafluoroborate and nitronium tetrafluoroborate in sulfolane solvent;

B. precipitating a sulfolane adduct; and

C. recrystallizing the alpha-form of the product from concentrated nitric acid.

28. A method of producing the beta-form of the product, beta-2,4,6,8,10,12-hexanitro-2,4,6,8,10,12-hexaazaisowurtzitane, comprising the steps of:

A. reacting 4,10-dibenzyl-2,6,8,12-tetraacetyl-2,4,6,8,10,12-hexaazaisowurtzitane sequentially with nitrosonium tetrafluoroborate and nitronium tetrafluoroborate in sulfolane solvent;

B. precipitating a sulfolane adduct; and

C. recrystallizing from benzene or a mixture of ethyl acetate and chloroform to produce the beta-form of the product.

* * * * *